(12) United States Patent
Igaue et al.

(10) Patent No.: US 7,125,400 B2
(45) Date of Patent: Oct. 24, 2006

(54) WEARING ARTICLE

(75) Inventors: Takamitsu Igaue, Mitoyo-gun (JP); Maki Watanabe, Mitoyo-gun (JP)

(73) Assignee: Uni-Charm Corporation, Shikokuchuo (JP)

( * ) Notice: Subject to any disclaimer, the term of this patent is extended or adjusted under 35 U.S.C. 154(b) by 74 days.

(21) Appl. No.: 10/849,938

(22) Filed: May 21, 2004

(65) Prior Publication Data

US 2004/0236303 A1 Nov. 25, 2004

(30) Foreign Application Priority Data

May 23, 2003 (JP) ............... 2003-146819

(51) Int. Cl.
 *A61F 13/62* (2006.01)
 *A44B 18/00* (2006.01)
 *A41B 9/00* (2006.01)

(52) U.S. Cl. ............ 604/385.03; 604/391; 2/114; 24/442

(58) Field of Classification Search ......... 604/385.01, 604/386–96, 385.03; 24/306, 442–52; 2/114
See application file for complete search history.

(56) References Cited

U.S. PATENT DOCUMENTS 5,897,545 A * 4/1999 Kline et al. ............ 604/386
6,524,293 B1 * 2/2003 Elsberg et al. .......... 604/385.13
6,730,069 B1 * 5/2004 Tanzer et al. ............ 604/391
2004/0006327 A1 * 1/2004 Karami ............... 604/391

FOREIGN PATENT DOCUMENTS

| JP | 64-061501 A | 3/1989 |
|----|-------------|--------|
| JP | 10-028703 A | 2/1998 |
| JP | 2977501 | 9/1999 |
| JP | 11-511671 A | 10/1999 |
| JP | 2000-506047 A | 5/2000 |
| JP | 2001-321399 A | 11/2001 |
| WO | WO-96/19960 A1 | 7/1996 |
| WO | WO-97/36566 A1 | 10/1997 |
| WO | WO 200035397 A1 * | 6/2000 |

* cited by examiner

*Primary Examiner*—Karin Reichle
(74) *Attorney, Agent, or Firm*—Morrison & Foerster LLP

(57) ABSTRACT

A wearing article such as a disposable diaper is provided in predetermined regions of the article with hook members. These predetermined regions are elastically stretchable at least in one direction. Each of the hook members includes a plurality of hook assemblies which are, in turn, attached to each of the predetermined regions so as to be spaced apart one from another in the one direction.

6 Claims, 5 Drawing Sheets

WEARING ARTICLE

BACKGROUND OF THE INVENTION

The present invention relates to wearing articles such as disposable diapers, disposable gowns used in medical field or bandages and particularly to such wearing articles utilizing a mechanical fastener.

Disposable wearing articles utilizing a mechanical fastener are well known in the art. For example, a disposable diaper disclosed in Japanese Patent Publication No. 2977501 utilizes a pair of Y-shaped tape fasteners extending outward from respective wings of a rear waist region in a transverse direction of the diaper. Each of these tape fasteners is provided on the inner surface at its distal end portion with a hook member of the tape fastener serving to cooperate with a loop member to form the entire tape fastener.

In the diaper disclosed in Japanese Patent Publication No. 2977501, respective proximal end portions of the Y-shaped tape fasteners are bonded to inner and outer surfaces of the respective wings. Such manner of bonding ensures that the tape fasteners can be permanently bonded to the wings, on one hand, but this locally stiffens the wings in zones thereof in which the tape fasteners are bonded thereto, on the other hand. For the diaper in which the wings should have elastic stretchability, this stretchability is deteriorated by the tape fasteners. In addition, the distal end portions of the tape fasteners already have a relatively high stiffness due to the presence of the hook member attached thereto and, in zones of the wings in which the respective hook members come in engagement with the loop member, the wings have a further higher stiffness which deteriorates stretchability and flexibility of the diaper.

SUMMARY OF THE INVENTION

In view of the problem described above, it is an object of the present invention to provide wearing articles such as disposable diapers that are improved to reduce or eliminate the deterioration of desired stretchability and flexibility of the wearing article due to the presence of the hook member as a component of the mechanical fastener.

According to the present invention, there is provided a wearing article comprising first and second surfaces opposed to each other when worn, the first and second surfaces releasably connected to each other by means of a mechanical fastener which comprises a hook member and a loop member.

The first surface is provided in a predetermined region with the hook member and the second surface is provided in a predetermined region with the loop member; the first surface is elastically stretchable at least in one direction in the predetermined region and in a vicinity thereof; the hook member comprises a plurality of hook assemblies each comprising a relatively stiff base sheet and one or more hooks rising from the base sheet; and the plurality of hook assemblies are attached to the first surface in the predetermined region so that the hook assemblies are spaced apart one from another in the one direction.

The present invention may include the following preferable embodiments.

The plurality of hook assemblies attached to the first surface are spaced apart one from another not only in the one direction but also in a direction crossing the one direction.

The plurality of hook assemblies are provided on a non-stretchable carrier sheet interposed between the assemblies and the predetermined region. The carrier sheet, in turn, is attached to the first surface in the predetermined region. The carrier sheet is tearable off between each pair of the hook assemblies being adjacent in the one direction as the carrier sheet is pulled together with the predetermined region in the one direction, allowing the predetermined region to be elastically stretched.

The wearing article is an open type diaper in which the first surface corresponds to an inner surface of the diaper, the predetermined region corresponds to each of wings formed in the diaper and the one direction corresponds to a transverse direction of the diaper in the wings.

The second surface corresponds to an outer surface of the diaper.

The first surface and the second surface also correspond to inner surface and outer surface of the wings of the diaper, which may be formed from an elastically stretchable nonwoven fabric and which thereby may also serve as the loop member.

The base sheet of the hook assembly is attached to the first surface over an area in a range of 2 to 200 mm$^2$.

The plurality of hook assemblies are spaced one from another by a distance in a range of 1 to 5 mm in the one direction.

The wearing article according to the present invention is primarily characterized in that the hook member as one part of the mechanical fastener comprises a plurality of hook assemblies attached to the article in the region which is elastically stretchable at least one direction so that these assemblies are spaced apart one from another in this one direction. Such an arrangement prevents the elastic stretchability desired for this region from being deteriorated due to the presence of the hook member.

DETAILED DESCRIPTION OF THE PREFERRED EMBODIMENTS

Details of a wearing article according to the present invention will be more fully understood from the description of a disposable diaper as one embodiment of the invention given hereunder with reference to the accompanying drawings.

Figure 1:
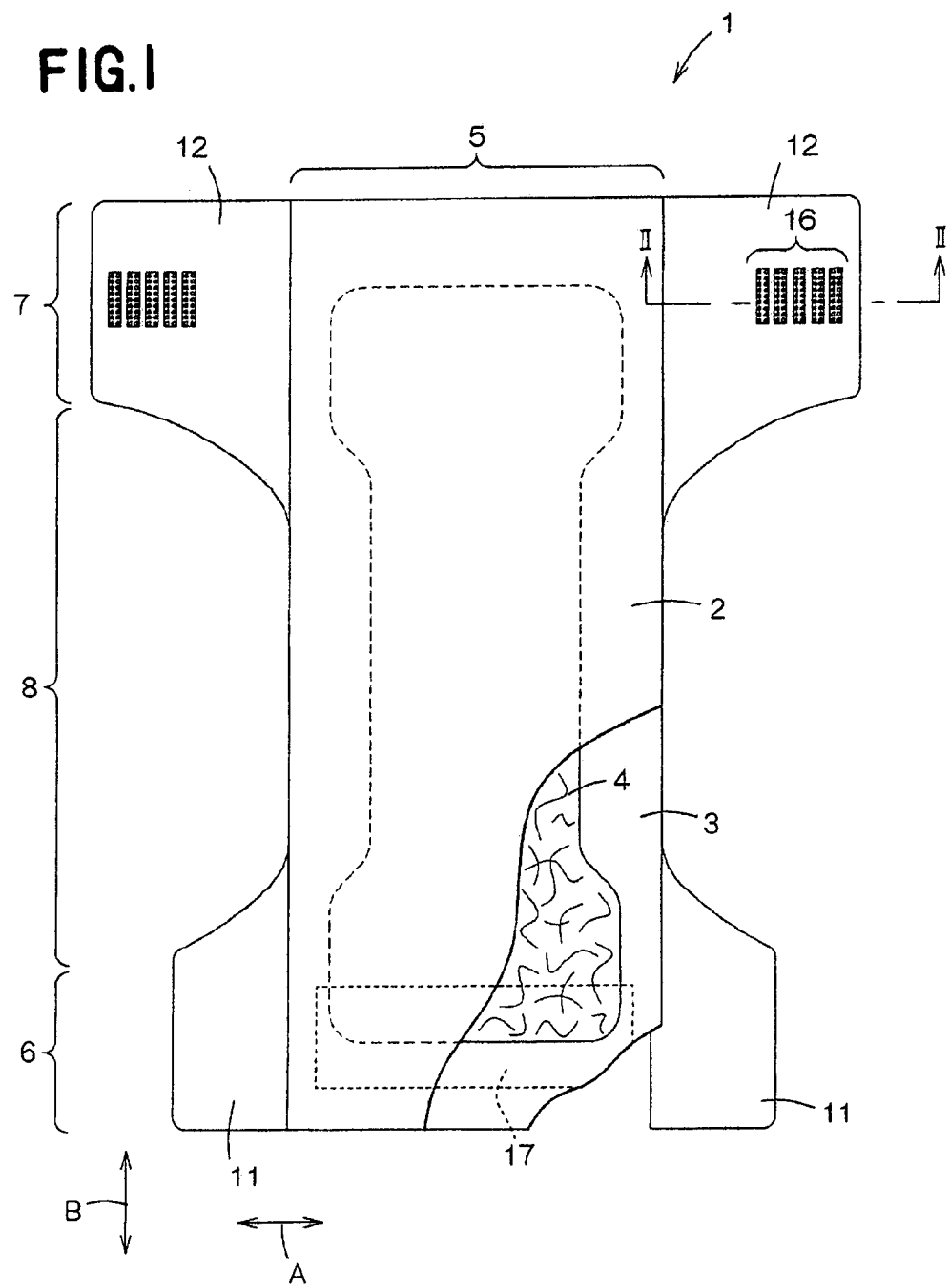
FIG. 1 is a partially cutaway plan view showing a diaper, a first embodiment of the invention.

A disposable diaper 1 as a first embodiment of the invention shown in FIG. 1 in a partially cutaway plan view is the so-called open-type diaper generally hourglass-shaped. The diaper 1 includes a region 5 lying in a middle as viewed in a transverse direction indicated by a double-headed arrow A and this middle region 5 comprises a liquid-pervious topsheet 2, a liquid-impervious backsheet 3 and a body fluid absorbent core 4 interposed between these two sheets 2, 3. In this middle region 5, portions of these top- and backsheets 2, 3 extending outward belong a peripheral edge of the core 4 are overlapped and bonded together by means of hot melt adhesives (not shown). As viewed in a longitudinal direction indicated by a double-headed arrow B, the diaper 1 has a front waist region 6, a rear waist region 7 and a crotch region 8 extending between these two regions. The front and rear waist regions 6, 7 are respectively provided with a pair of front wings 11 and a pair of rear wings 12 both pairs extending outward from the middle region 5 of the diaper 1 in the transverse direction A. These wings 11, 12 have their proximal end portions bonded to the outer surface of the backsheet 3 by means of hot melt adhesives (not shown). Of these wings 11, 12, at least the rear wings 12 are elastically stretchable at least in the transverse direction A. The rear wings 12 are respectively provided on inner surfaces thereof with a hook member 16 serving as a fastening means to connect the front and rear waist regions 6, 7 with each other. The backsheet 3 defining the front waist region 6 in the middle region 5 of the diaper 1 is provided on its outer surface with a loop member 17 with which the hook members 16 are releasably engaged.

Figure 2:
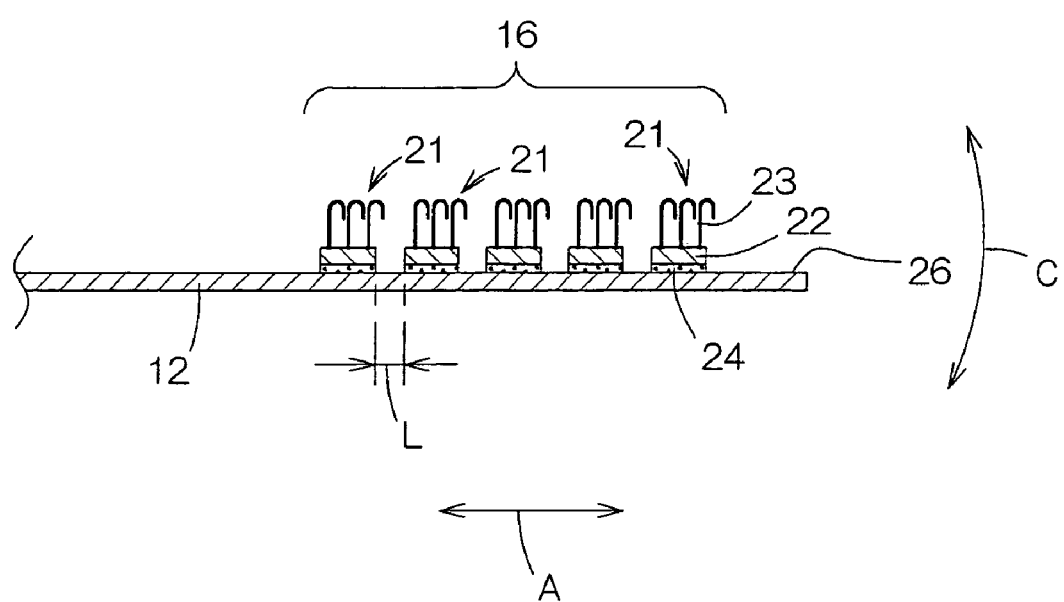
FIG. 2 is a sectional view taken along the line II—II in FIG. 1.

FIG. 2 is a sectional view taken along the line II—II in FIG. 1. As illustrated, the hook member 16 provided on the inner surface of each of the rear wings 12 comprises a plurality of independent hook assemblies 21. Each of the assemblies 21 has a stiffness higher than that of the rear wing 12 and comprises a non-stretchable base sheet 22 and at least a single hook 23 rising up on the base sheet 22. The base sheet 22 is attached to the rear wing 12 by a suitable bonding means such as adhesives 24. Each pair of the hook assemblies 21 being adjacent in the transverse direction A are spaced apart from each other by a first distance L. The rear wing 12 carrying the hook assemblies in this manner is elastically stretched as it is pulled in the transverse direction A with its outer side edges 26 held by a wearer's fingers. Thereupon, each pair of the adjacent hook assemblies 21 of the hook member 16 are spaced apart from each other by a stretched distance $L_2$ and, in this state, come in engagement with the loop member 17. In FIG. 2, an area over which each of the hook assemblies 21 is attached to the rear wing 12 is in a range of 2 to 200 $mm^2$ and the distance L is in a range of 1 to 5 mm in order to avoid an anxiety that the hook member 16 might deteriorate the desired stretchability and flexibility of the rear wing 12. Preferably at least three hook assemblies 21 are arranged in the transverse direction A so that the front and rear waist regions 6, 7 may be firmly connected together when the diaper 1 is worn. A plurality of the hook assemblies 21 spaced apart one from another by the distance L allows the respective rear wings 12 to be smoothly curved in a wearer's waist surrounding direction indicated by a double-headed arrow C in FIG. 2 substantially without an affection by the hook members 16 provided on the respective rear wings 12. In addition, the hook members 16 are engaged with the loop member 17 as the rear wings 12 are being stretched in the transverse direction A and therefore each pair of the adjacent hook assemblies 21 can be further spaced apart from each other by the distance $L_2$ enough to protect the flexibility of the rear wings 12 from being affected by the hook members 16.

Figure 3:
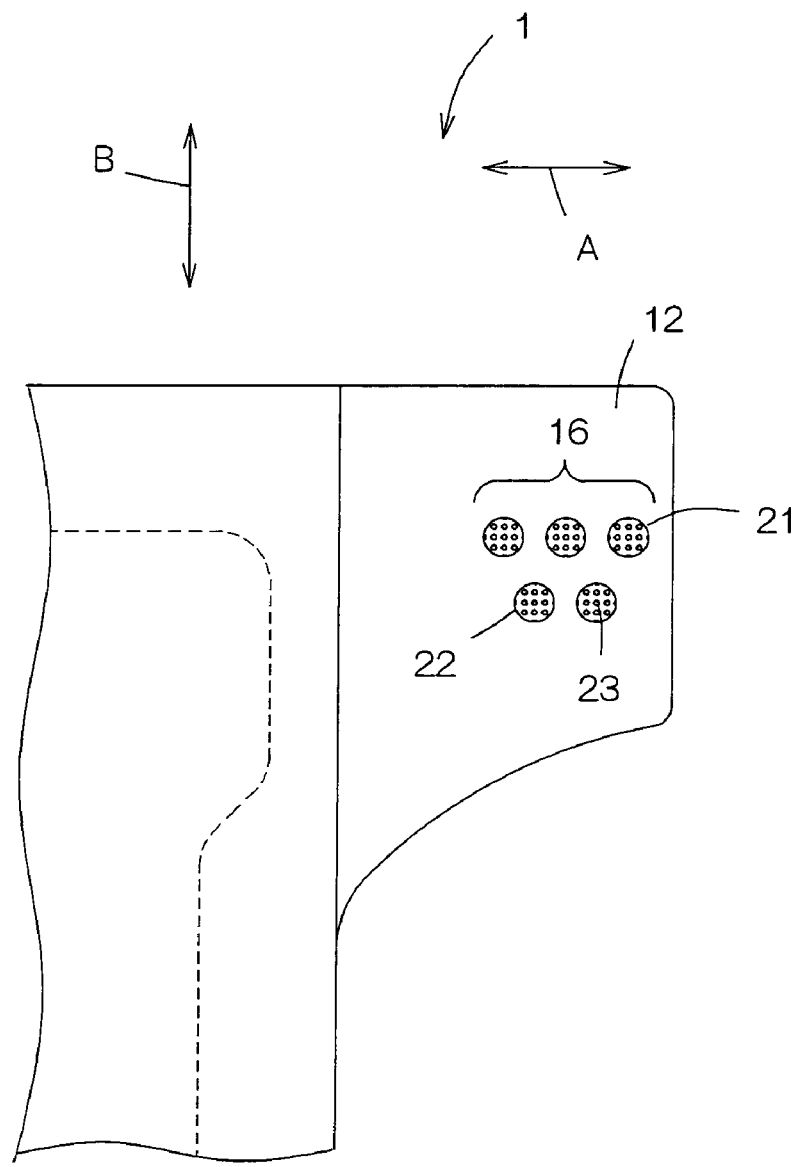
FIG. 3 is a partial view showing a diaper according to a second embodiment of the invention similar to the diaper 1 of FIG. 1.

FIG. 3 is a partial view showing a diaper 1 according to a second embodiment of the invention similar to the first embodiment of the invention in FIG. 1. In this diaper 1, each of the hook assemblies 21 constituting the hook member 16 includes the base sheet 22 having a circular planar shape. One or more hooks 23 rise up on this base sheet 22. A plurality of the hook assemblies 21 are spaced apart one from another not only in the transverse direction A but also in the longitudinal direction B. It is unlikely that these hook assemblies 21 might deteriorate the elastic stretchability in the transverse direction as well as in the longitudinal direction, which is desired for the rear wings 12.

Figure 4:
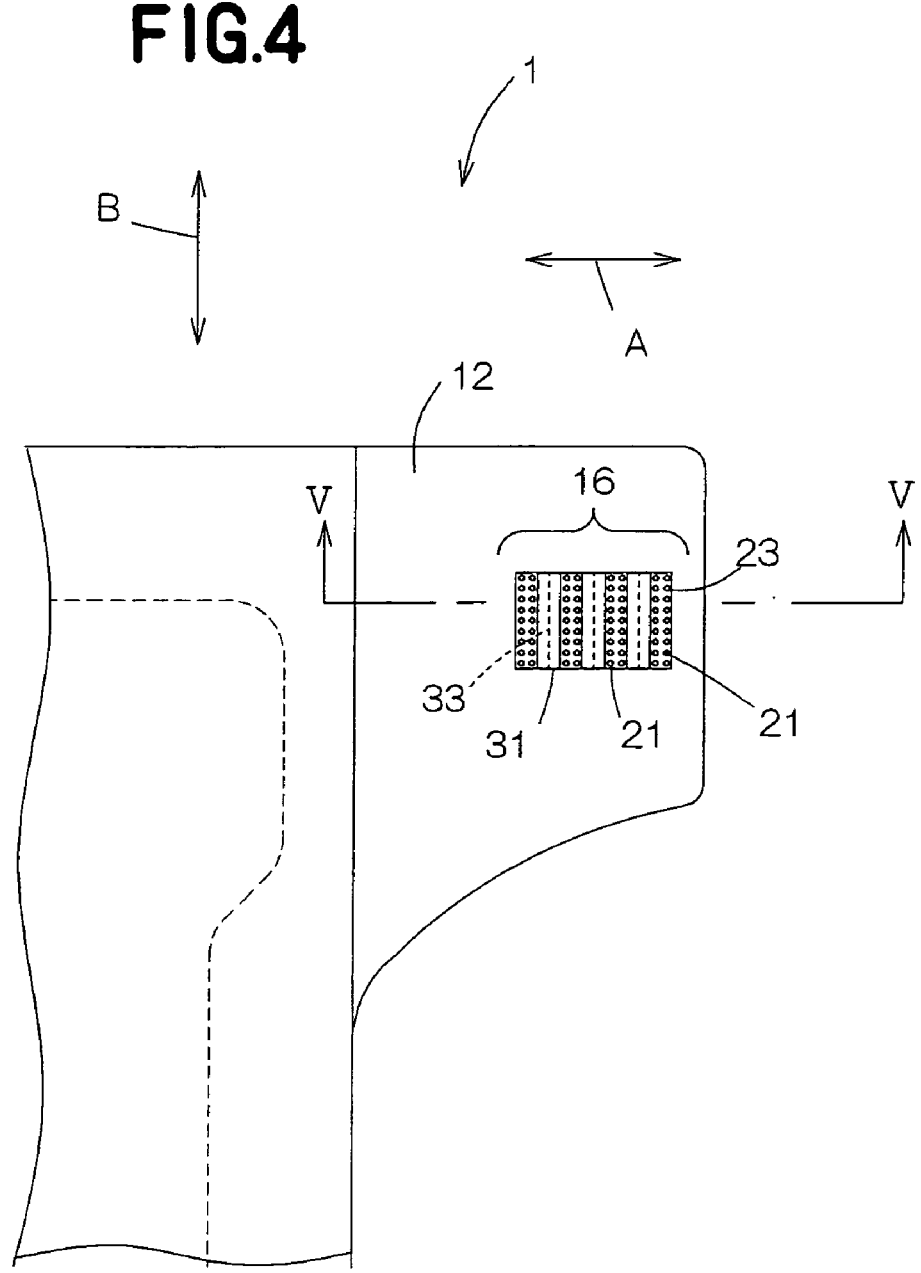
FIG. 4 is a view similar to FIG. 1 partially showing a third embodiment of the invention.
Figure 5A:
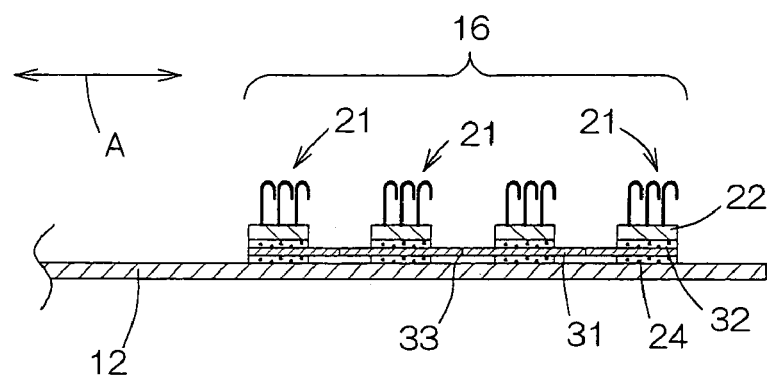
FIGS. 5A–B are sectional views taken along the line V—V in FIG. 4 in a non-stretched state (A) and in a stretched state (B).
Figure 5B:
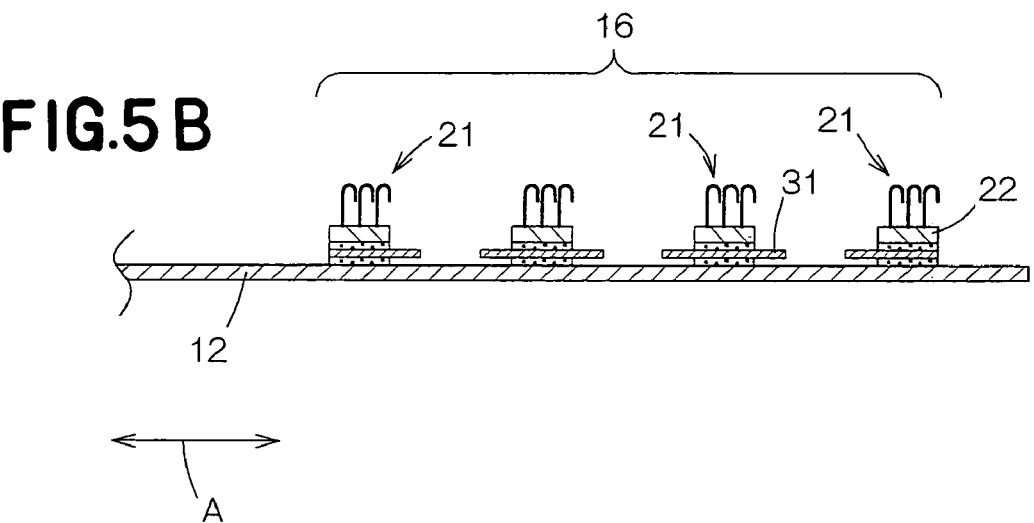

FIGS. 4 and 5A–B illustrate a third embodiment of the invention wherein FIG. 4 partially shows a diaper similar to that of FIG. 1 and FIGS. 5A–B are a sectional view taken along the line V—V in FIG. 4. FIG. 5 illustrates the rear wing 12 in its non-stretched state (A) and in its stretched state (B). In the hook member 16 provided on the rear wing 12 of this diaper 1, the individual base sheets 22 carrying thereon the individual hook assemblies 21 are spaced apart one from another in the transverse direction and, in this state, bonded to the carrier sheet 31 by means of adhesives 32. The carrier sheet 31 is, in turn, bonded to the rear wing 12 by means of adhesives 24 applied on this carrier sheet 31 at its zones immediately underlying the respective hook assemblies 21. The carrier sheet 31 is non-stretchable and not bonded to the rear wing 12 between each pair of the adjacent hook assemblies 21, 21. Between each pair of the adjacent hook assemblies 21, 21, the carrier sheet 31 is provided with tear-off lines 33 extending in the longitudinal direction B. The tear-off lines 33 may be provided in the form of perforations or slits along which the carrier sheet 31 can be easily torn off as the rear wing 12 is pulled in the transverse direction A. The carrier sheet 31 torn off along the respective tear-off lines 33 is shown in FIG. 5 (B). The hook member 16 shown in FIG. 5 (A) not only provides the same effect as the hook member 16 shown in FIGS. 1 through 3 but also allows the diaper 1 to be manufactured such that the individual hook assemblies 21 are previously bonded to the carrier sheet 31 and then this carrier sheet 31 is bonded to the rear wing 12. This process allows the hook assemblies 21 to be bonded to the rear wing 12 even if these assemblies 21 are relatively small.

In the diaper 1 illustrated herein, the respective members such as the topsheet 2, the backsheet 3 and the core 4 may be formed using stock materials well known to those skilled in the art. The outermost layer of the backsheet 3 may be formed by nonwoven fabrics, more preferably by relatively bulky nonwoven fabrics to eliminate the requirement for separate loop member 17 as shown in FIG. 1 because the hooks of the hook member 16 can be releasably engaged with such nonwoven fabrics. If the front wings 11 are formed by such nonwoven fabrics, the hooks 23 can be releasably engaged also with the front wings 11. The rear wings 12 may be formed, for example, using nonwoven fabrics containing therein elastic fibers or films made of plastic elastomers. The carrier sheet 31 may be formed, for example, using materials of plastic film, fabric or paper in which a molecular chain or fiber is oriented in the longitudinal direction B. In this case, the torn-off lines 33 may be eliminated.

The present invention having been described with respect to the disposable diaper as the embodiments is applicable also to the other various wearing articles such as disposable gowns used in medical site and bandages.

What is claimed is:
1. A wearing article comprising:
   first and second surfaces opposed to each other when worn, said first and second surfaces being releasably connectable to each other by a mechanical fastener comprising a hook member and a loop member;
   said first surface being provided in a first predetermined region with said hook member and said second surface being provided in a second predetermined region with said loop member;

said first surface being elastically stretchable at least in one direction in said first predetermined region and in a vicinity thereof;

said hook member comprising a plurality of hook assemblies each comprising a relatively stiff base sheet and one or more hooks rising up from said base sheet; and said plurality of hook assemblies being attached to said first surface in said first predetermined region so that said hook assemblies are spaced apart one from another in said one direction; and wherein said plurality of hook assemblies are provided on a non-stretchable carrier sheet, said carrier sheet is attached to said first surface in said first predetermined region interposed between said first predetermined region and the plurality of hook assemblies; and said carrier sheet is tearable off between each adjacent pair of said hook assemblies as said carrier sheet and said first predetermined region are pulled in said one direction allowing said first predetermined region to be elastically stretchable.

2. The wearing article according to claim 1, wherein said wearing article is an open type diaper comprising a first pair of wings, and wherein said first surface corresponds to an inner surface of said diaper, said first predetermined region is located on an inner surface of said first pair of wings, and said one direction corresponds to a transverse direction of said diaper.

3. The wearing article according to claim 2, wherein said second surface corresponds to an outer surface of said diaper, and comprises an elastically stretchable nonwoven fabric, said loop member also comprising said elastically stretchable nonwoven fabric.

4. The wearing article according to claim 1, wherein said second surface corresponds to an outer surface of said article.

5. The wearing article according to claim 1, wherein each of said base sheets of said plurality of hook assemblies is attached to said first surface over an area in a range of 2 to 200 mm$^2$.

6. The wearing article according to claim 1, wherein said plurality of hook assemblies are spaced apart one from another by a distance in a range of 1 to 5 mm in said one direction.

* * * * *